(12) United States Patent
Pfaffinger et al.

(10) Patent No.: US 9,492,242 B2
(45) Date of Patent: Nov. 15, 2016

(54) CLEANING OR CARE DEVICE FOR MEDICAL OR DENTAL INSTRUMENTS

(75) Inventors: Nikolaus Pfaffinger, St. Pantaleon (AU); Christian Spieler, Michaelbeuern (AU)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 1102 days.

(21) Appl. No.: 13/583,576

(22) PCT Filed: Mar. 2, 2011

(86) PCT No.: PCT/EP2011/053067
§ 371 (c)(1),
(2), (4) Date: Oct. 25, 2012

(87) PCT Pub. No.: WO2011/110452
PCT Pub. Date: Sep. 15, 2011

(65) Prior Publication Data
US 2013/0092192 A1    Apr. 18, 2013

(30) Foreign Application Priority Data
Mar. 8, 2010  (EP) .................................... 10155736

(51) Int. Cl.
| | | |
|---|---|---|
| *B08B 9/00* | (2006.01) | |
| *B08B 9/02* | (2006.01) | |
| *A61C 19/00* | (2006.01) | |

(52) U.S. Cl.
CPC ............. *A61B 90/70* (2016.02); *A61C 19/002* (2013.01); *B08B 9/02* (2013.01)

(58) Field of Classification Search
CPC .................................................. A61C 19/002
See application file for complete search history.

(56) References Cited

U.S. PATENT DOCUMENTS

2006/0196728 A1   9/2006  Numakawa et al.
2007/0031778 A1   2/2007  Helfenbein et al.

FOREIGN PATENT DOCUMENTS

| EP | 1683499 A1 | 7/2006 |
| WO | WO/9415547 | * 7/1994 |
| WO | WO/2008007987 | * 1/2008 |
| WO | WO2010/016066 A1 | 2/2010 |

OTHER PUBLICATIONS

Machine translation of WO/9415547 by Rosenstatter, published Jul. 21, 1994.*
International Search Report of the International Searching Authority, mailed Jun. 9, 2011, for corresponding International Application No. PCT/EP2011/053067, 9 pages.

* cited by examiner

*Primary Examiner* — Michael Kornakov
*Assistant Examiner* — Ryan Coleman
(74) *Attorney, Agent, or Firm* — Klarquist Sparkman, LLP

(57) ABSTRACT

A cleaning or care device for the cleaning or care of medical or dental instruments, having a cleaning or care chamber in which at least two connections for the instruments to be cleaned are provided, and a supply device for supplying the at least two connections with a cleaning or care agent. The at least two connections and the supply device can be moved relative to one another in such a way that one of the connections can be connected to the supply device and supplied with a cleaning or care agent, while another of the connections is not connected to the supply device and cannot be supplied with a cleaning or care agent. A corresponding method for the cleaning or care of medical or dental instruments with such a cleaning or care device is also described.

17 Claims, 4 Drawing Sheets

CLEANING OR CARE DEVICE FOR MEDICAL OR DENTAL INSTRUMENTS

CROSS REFERENCE TO RELATED APPLICATION

This is the U.S. National Stage of International Application No. PCT/EP2011/053067, filed Mar. 2, 2011, which in turn claims the benefit of European Patent Application No. EP10155736.1, filed Mar. 8, 2010. Both applications are incorporated herein by reference.

BACKGROUND

1. Field

The present invention concerns a cleaning or care device for the cleaning or care of medical instruments, particularly dental instruments, and a corresponding cleaning or care method.

2. Description of Prior Art

Such a cleaning or care device is known, for example, from patent application US 2007/0031778 A1. It comprises a cleaning chamber in which two or more connections are provided for the instruments to be cleaned. This provision of two or more connections advantageously permits multiple instruments to be cleaned or cared for in a single cleaning or care cycle.

The disadvantage of this cleaning or care device is that with each additional connection the structure of the cleaning or care device and the control of the cleaning or care device become more complicated, since each connection needs, for example, to be connected to the sources of the cleaning, care and/or rinsing agents by its own supply devices, particularly its own lines or line sections, since for each connection a separate actuator, controller, or sensors are required. This means that the volume of the cleaning or care device also increases disadvantageously, so that cleaning or care devices with multiple connections for the instruments to be cleaned are often very voluminous and bulky.

The present application therefore has the remit of providing a cleaning and care device for the cleaning or care of medical instruments, particularly dental instruments, which, while retaining the advantage that multiple instruments can be cleaned or cared for during one cleaning or care cycle, still has a simpler structure of the supply device and consumes less space.

SUMMARY

This task is resolved, according to one embodiment, by a cleaning or care device for the cleaning or care of medical, instruments, particularly dental instruments, comprising: A cleaning or care chamber, particularly one which can be closed, in which at least two connections are provided for, for the instruments to be cleaned, as well as a supply device for supplying said at least two connections with a cleaning or care agent, wherein said at least two connections and the supply device can be moved relative to one another in such a way that (optionally) one of said at least two connections is connected to the supply device and can be supplied with a cleaning and/or care agent, while another of said at least two connections is not connected to the supply device and is not supplied with a cleaning and/or care agent. According to different embodiments, either said at least two connections can be moved relative to the supply device and/or the supply device can be moved relative to said at least two connections.

Due to the option of moving said two or more connections and the supply device relative to one another, and thus connecting the connections, one after the other, to the supply device or supplying them, one after the other, with the cleaning and/or care agent(s), it is therefore no longer necessary to provide each connection with its own supply devices, particularly its own lines or line sections, actuators, controllers, sensors, etc. Instead, the number of at least one of such elements can be less than the number of connections.

In accordance with a preferred embodiment, the cleaning or care device has a single supply device, with which one connection at a time can be connected to the supply device, leaving all the other connections disconnected. In particular, the cleaning or care device or the supply device comprises a single interface or transition point for the optional coupling or connection of one of said at least two connections at which the cleaning and/or care agent(s) are consigned. Obviously, multiple lines for cleaning and/or care agents can be provided for or bundled at this interface. The interface preferably has at least one opening for a cleaning fluid and at least one opening for a lubricant.

According to one embodiment, the supply device is fluidly connected to said at least two connections, particularly via at least one passage or at least one line, so that said at least two connections can be supplied with one or more cleaning and/or care agents. The passage or the line can, if necessary, bridge or run through the interface or transition point mentioned above. Said at least two connections are preferably designed in such a way that they dispense or pass on the cleaning and/or care agents received from the supply device through one or more openings. The supply lines of the instruments to be cleaned or cared for can, as an explicit preference, be coupled with this opening or these openings in such a way that the interior of the instruments to be cleaned or cared for, particularly its supply lines, can be supplied via said at least two connections with a cleaning or care agent.

A cleaning or care device within the meaning of the present brief is any device that dispenses at least one cleaning and/or care agent to a medical instrument, particularly a dental instrument, in order to clean it, disinfect it, sterilize it, free it from any contamination or microorganisms, or care for it. The cleaning and/or care agent may, for example, be a liquid, particularly hot or cold water, steam, a disinfectant or sterilization agent, a gas, for example compressed air, or a lubricant, for instance natural or synthetic lubricating oils.

The medical instruments, particularly dental instruments, are understood to be in particular straight and contra-angled handpieces for driving a variety of tools, such as rotating drills, tartar removal tools, files, saws, reamers, etc., handpieces for dispensing medical materials, such as fillers or anesthetics, functional handpieces for providing light, water or air, and non-driven hand instruments, such as endoscopes, etc.

According to one embodiment, said at least two connections are arranged on a common base element that can be moved relative to the supply device and positioned in such a way that, optionally, one of said at least two connections is connected to the supply device, while another of said at least two connections is not connected to the supply device. The base element is, as an explicit preference, implemented as a rotating element, that can be rotated relative to the supply device. The provision of a movable or rotating base element permits the cleaning or care device to be designed in a particularly compact and space-saving way.

According to an alternative embodiment, said at least two connections are substantially arranged in a line, and the supply device or parts thereof, particularly the coupling parts that can be connected to the connections, can be moved along said line, for which purpose preferably a linear motor is provided for.

According to one embodiment, the cleaning or care device is implemented as an automated cleaning or care device with a drive motor for the relative movement of said at least two connections and/or the supply device. The drive motor is preferably located outside the cleaning or care chamber. It comprises, for example, an electric motor, particularly a stepper motor. The use of a stepper motor is, due to its reliability and simple control, of particular advantage for the present invention. The drive motor is, as an explicit preference, connected via at least one drive element, for example a belt drive and/or a shaft, to said at least two connections and/or the supply device and/or the base element.

According to another embodiment, the cleaning or care device comprises a distributor provided for between the movable or rotating base element and the supply device to pass on a cleaning and/or care agent from the supply device to said at least two connections, wherein the distributor has a first distributor part that can be moved with the base element relative to the supply device and a second distributor part that is fixed relative to the supply device. This structure ensures a particularly reliable transfer of the cleaning and/or care agent to the base element. The first distributor part preferably comprises at least one separate line or line section for each of said at least two connections. The second distributor part comprises at least one line for a cleaning and/or care agent, wherein the motion of the base element, and thus of the first distributor part, relative to the second distributor part can connect the lines of the first distributor part with said at least one line of the second distributor part. This fluid-carrying connection can thus be used to transfer the cleaning and/or care agent or agents from the supply device to the connections and to the instruments to be cleaned coupled to the connections.

If the base element is designed as a rotating element, then, according to a preferred embodiment, it is of particular advantage to form the first and second distributor parts as a disk, wherein each distributor part has one outer sheath surface and two sliding surfaces, and wherein the two distributor parts are arranged so that they slide one on the other via one of their sliding surfaces. The two disk-shaped distributor parts thus form a sliding bearing, on which the rotating element is supported rotatably.

According to another embodiment, there is a detector unit on the cleaning or care device for positioning the base element in a predefined starting position. The detector unit preferably has a mark on a drive element connecting the drive motor to the base element, and a sensor that detects the mark. Such a detector unit is particularly advantageous when the base element can be turned manually, for example to simplify coupling the instruments to be cleaned with the connections. Once the instruments have been coupled, the base element is in a random or undefined position. To be able to connect one of the connections with the supply device in such a way that fluid is conveyed during the subsequent cleaning or care procedure, the base element is first moved into the predefined starting position using the detector unit, and then, from this starting position, one of the connections is coupled to the supply device. This ensures a reliable connection between the connections and the supply device without requiring increased control system expenditure.

The detector unit may, for example, comprise a radiation source, particularly a light source, a projection on a shaft of the drive motor that serves as a mark, and an optical sensor that detects blocking of the light source by the projection, wherein the covering of the light source marks the starting position. According to another example, the marking is implemented as a magnetic element on a shaft of the drive motor, and the sensor as a magnetic sensor.

According to one embodiment, the cleaning or care device comprises a detector unit to determine which of said at least two connections is occupied by a medical instrument, particularly a dental, instrument and/or which of said at least two connections is not occupied by a medical instrument, particularly a dental, instrument, and to emit corresponding occupation signals for each of said at least two connections, wherein the detector unit is connected to a control system that is designed, based on the occupation signals emitted by the detector unit, only to supply those of said at least two connections with cleaning and/or care agents to which a medical instrument, particularly a dental instrument, is connected. The detector unit comprises, for example, a radiation source, particularly a light source, that emits a radiation into the cleaning or care chamber, and an optical sensor that detects a weakening or interruption of the radiation emitted into the cleaning or care chamber caused by an instrument coupled to a connection. If a connection is empty, i.e., is not occupied by an instrument, then, according to a preferred embodiment, the controller drives the drive motor in such a way that it does not stop when the empty connection is connected to the supply device, but rather continues to run so that the base element is moved further until the next connection occupied by an instrument is connected to the supply device.

According to another embodiment, two nozzles placed independently or separately from said at least two connections are provided for on the cleaning or care device for dispensing a cleaning and/or care agent onto the outside of the medical, particularly dental instruments. Said at least two connections are preferably implemented in such a way that they convey a cleaning and/or care agent into the interior of the medical instruments, particularly dental instruments.

A method for the cleaning or care of medical instruments, particularly dental instruments, with a cleaning or care device described in the present publication is defined by one of said at least two connections being connected to the supply device and supplied by the supply device with a cleaning and/or care agent, while another of said at least two connections is not connected to the supply device and receives no cleaning and/or care agent from the supply device. In particular, said at least two connections are successively connected to the supply device and supplied by the supply device with a cleaning and/or care agent, so that at least a part of the cleaning or care method, in particular the cleaning or care of the interior of the medical instruments, particularly dental, instruments, is carried out sequentially. The method furthermore preferably comprises the feature of only those of said at least two connections being connected to the supply device and supplied with a cleaning and/or care agent by the supply device that are occupied by a medical instrument, particularly a dental instrument.

According to another embodiment, cleaning or care method is designed in such a way that first the interior cleaning or care of all the instruments is carried out, and subsequently the exterior cleaning or care of the instruments. This reduces the risk of mutual contamination of the instruments, in particular contamination of an instrument already cleaned on the exterior, by contaminated cleaning fluid being sprayed from the interior of another instrument. The nozzles for the exterior cleaning or care are preferably arranged in the cleaning or care device in such a way that essentially only one connection or one instrument connected with it is exposed to cleaning and/or care agents, while at least a second connection or second instrument connected to it is essentially not exposed to cleaning and/or care agents. A cleaning or care method that includes interior and exterior cleaning or care would accordingly be carried out in such a manner that, for the interior cleaning or care, first of all each of said at least two connections is successively connected to the supply device in order to convey cleaning and/or care agents into the interior of the instruments, and then each of said at least two connections is successively positioned relative to the nozzles in such a way that the exterior cleaning or care of the individual instruments is carried out. Alternatively, it is, of course, also possible to move the nozzles for the exterior cleaning sequentially to the respective instruments or relative to said at least two connections.

The invention will now be explained on the basis of preferred embodiments and making reference to the accompanying drawings:

DETAILED DESCRIPTION

Figure 1:
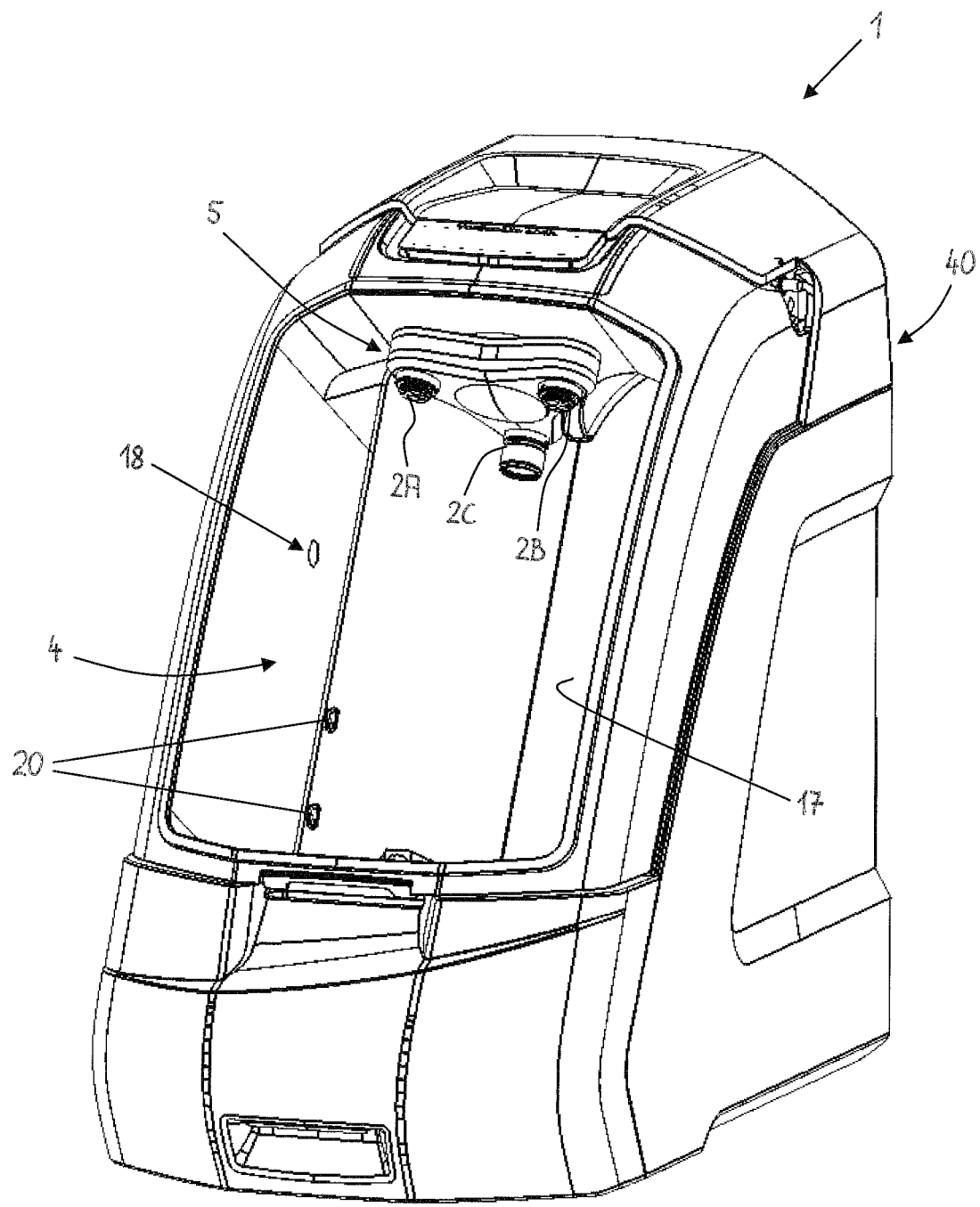
FIG. 1 shows an exterior view of an embodiment of a cleaning or care device, where the connections for the instruments to be cleaned and the supply device can be moved relative to one another.
Figure 2:
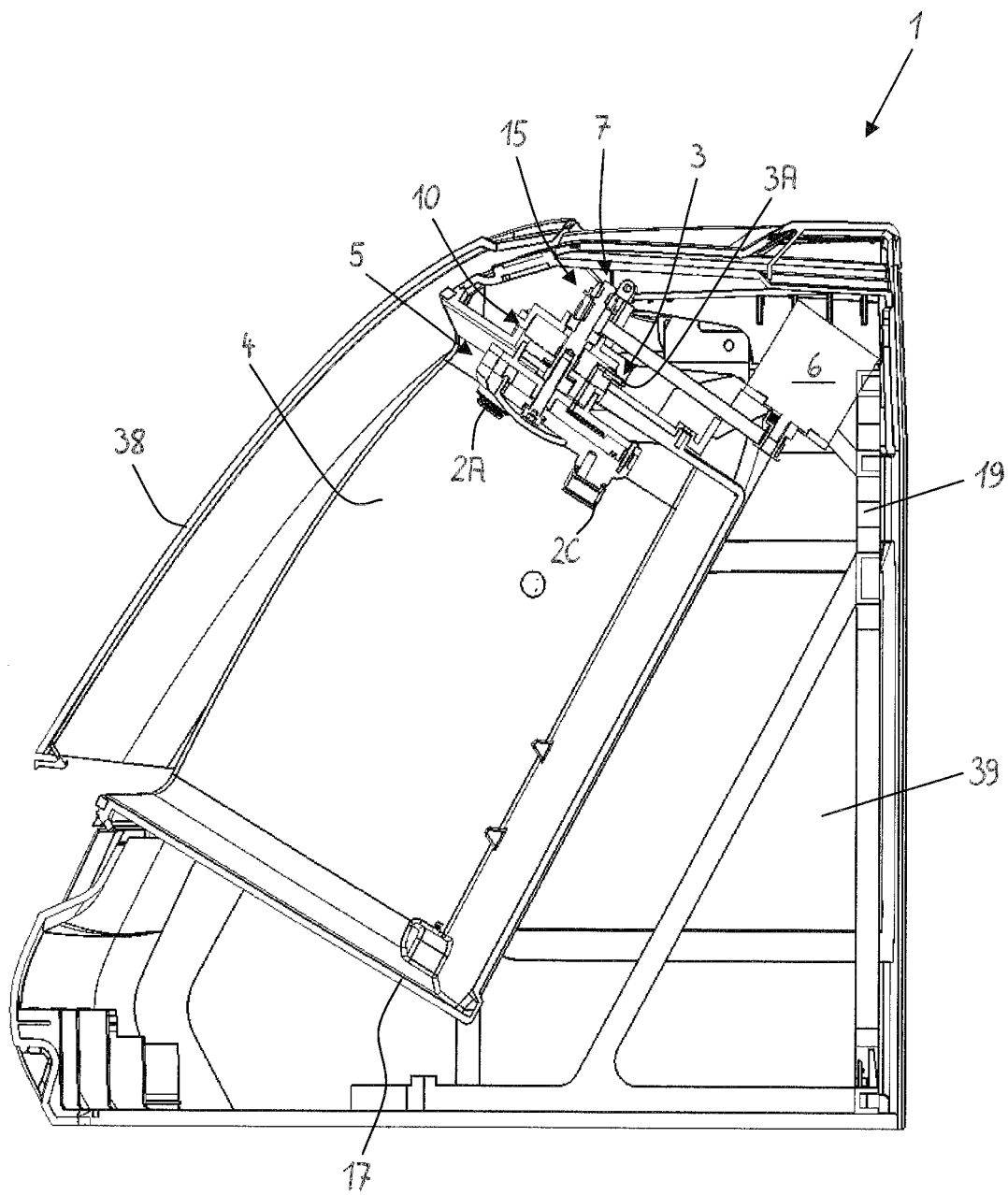
FIG. 2 shows a sectional representation of the cleaning or care device shown in FIG. 1.

The cleaning or care device 1 shown in FIGS. 1 and 2 comprises a housing 40, preferably made of plastic, with a base plate, multiple side walls, and a top plate. One of the side walls has a moving, particularly swiveling, door or a moving, particularly swiveling, cover 38, which can be moved, preferably by means of hinges on the top plate. The cover 38 selectively closes a cleaning or care chamber 4 located in the interior of the housing 40, in which multiple couplings or connections, in this case three connections 2A, 2B and 2C, are provided for, for medical instruments, particularly dental instruments, to be cleaned or cared for. By means of the connections 2A, 2B and 2C, one or more cleaning or care agents are conveyed into the interior of the instruments. Moreover, one or more openings or nozzles 20 are arranged in the cleaning or care chamber 4, through which a cleaning or care agent can be dispensed onto the outside of the instruments. The nozzles 20 are located separately from the connections 2A, 2B and 2C, and can be supplied with a cleaning and/or care agent independently of the nozzles 2A, 2B and 2C, particularly at independent times.

The cleaning or care chamber 4 is separated from a control chamber 39 (see FIG. 2) by a dividing wall 17 located in the interior of the cleaning or care device 1. On or in the control chamber 39 there are a variety of control and functional elements of the cleaning or care device 1, for example a supply device 3, of which, for reasons of clarity, only a short line section 3A is shown in FIG. 2, and which, among other things, may comprise containers for cleaning, care, or lubrication agents, connections to one or more fluid sources, for example to a compressed air or water source, lines to convey fluids, cleaning, care, or lubricating agents, pumps, controllers and actuators, for example valves, throttles, sensors, for example for flow measurement or concentration measurement; mixers and many other components. In addition to the supply device 3, there may be other components on or in control chamber 39, such as a connection to a power source, catch basins or drains for used cleaning or care agents, a control system 19 for the control and/or regulation of the cleaning or care process, a memory unit, a detector unit 15 for positioning connections 2A, 2B and 2C in a predefined starting position, an operating display, or a control panel for the user.

A detector unit 18 visible in FIG. 1 for determining which of the connections 2A, 2B and 2C is occupied by a medical instrument, particularly a dental instrument, and/or which of connections 2A, 2B or 2C is not occupied by a medical instrument, particularly a dental instrument, preferably comprises a radiation source, particularly for the emission of infrared radiation, and a sensor, particularly an infrared sensor, for detection of the radiation. The radiation source and the sensor are provided for on different sections of the dividing wall 17. The radiation source emits its radiation towards the sensor through the cleaning or care chamber 4. If an instrument is coupled to one of the connections 2A, 2B or 2C, then the radiation will be weakened or interrupted by the instrument, as a result of which the sensor will detect the presence of an instrument. The sensor generates corresponding occupation signals and emits them to the control system 19, which, based on such occupation signals, only supplies those connections 2A, 2B and 2C with cleaning or care agents to which a medical instrument, particularly a dental instrument, is connected.

The connections 2A, 2B and 2C and supply device 3 can be moved relative to one another in such a way that at least one of the connections 2A, 2B and 2C is connected to the supply device 3 and supplied with a cleaning or care agent, while at least another of the connections 2A, 2B and 2C is not connected to the supply device 3, nor is it supplied with a cleaning or care agent. To this end, the connections 2A, 2B and 2C are arranged on a base element 5 that can be moved relative to the supply device 3, which is in particular implemented as a rotating element that can be rotated relative to the supply device 3. The base element 5 is set in rotation by a drive motor 6 located in the control chamber 39, which is preferably implemented as a stepper motor, and one or more drive elements 7. The operation of the drive motor 6, for example the control of the number of steps of the stepper motor, is carried out using the control system 19, depending upon the cleaning or care program executed by the control system 19. The base element 5 can therefore be moved (rotated) relative to the supply device 3, and positioned in such a way that, optionally, one or only one of the connections 2A, 2B or 2C is connected to the supply device 3 and supplied with cleaning or care agents, while another of the connections 2A, 2B or 2C any other of the connections 2A, 2B or 2C is not connected to the supply device 3 and thus not supplied with cleaning or care agents.

The connections 2A, 2B and 2C are supplied with cleaning or care agents by a distributor 10 located between the base element 5 and the supply device 3.

Figure 3:
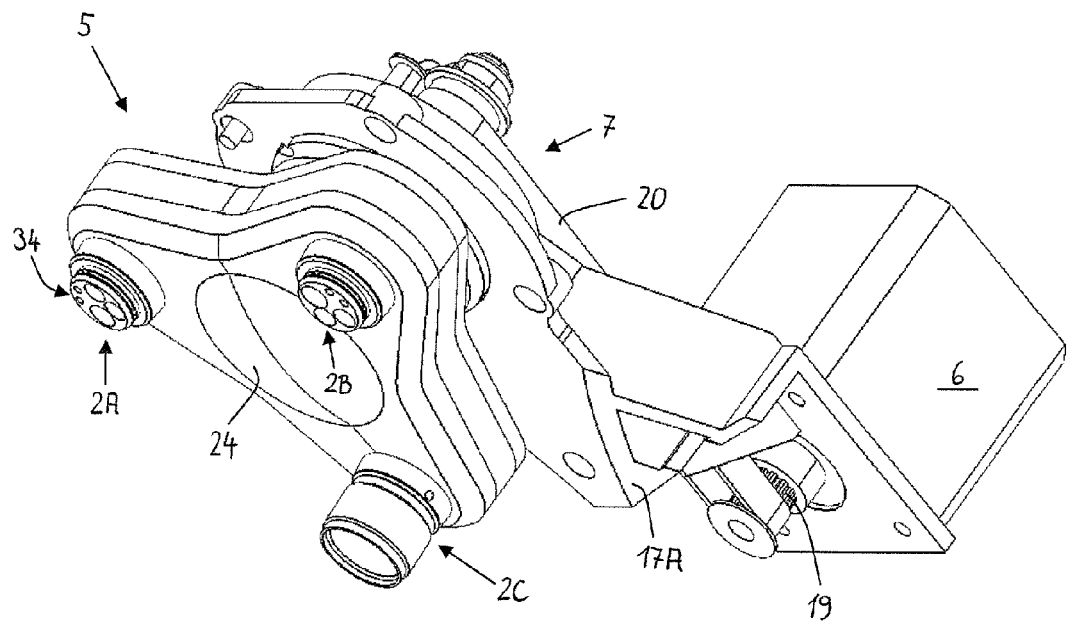
FIG. 3 shows a perspective view of an embodiment of a base element that can be moved, particularly rotated, relative to the supply device, with a distributor for a cleaning and/or care agent and a drive motor.
Figure 4:
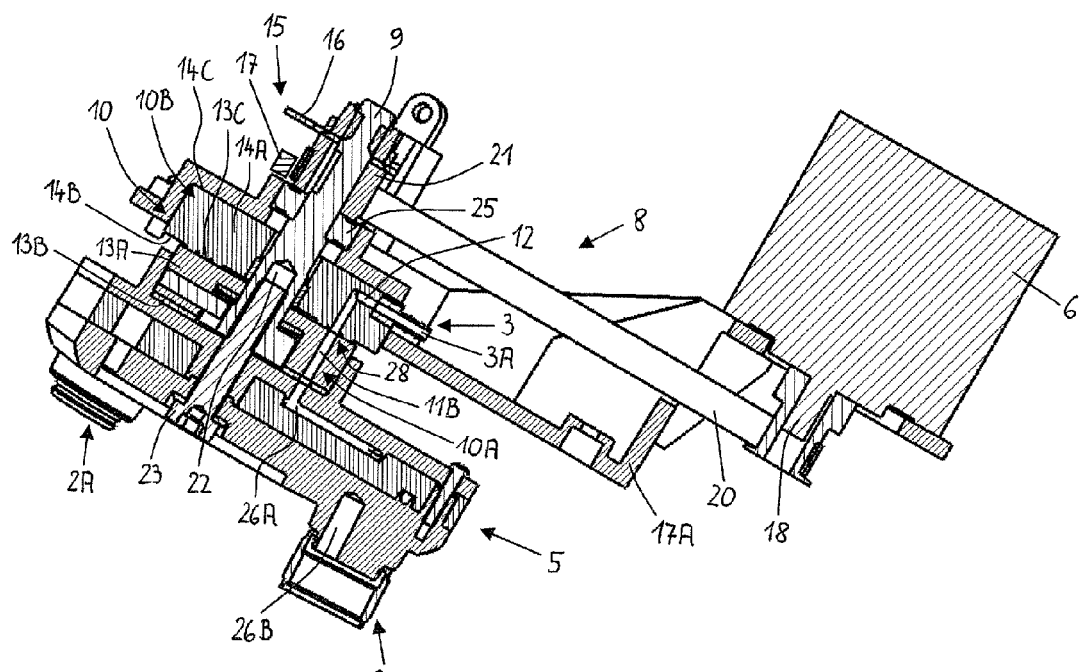
FIG. 4 shows a sectional representation of the base element, the distributor, and the drive motor shown in FIG. 3.

The base element 5, along with the connections 2A, 2B and 2C, the drive motor 6 with the drive elements 7, the detector unit 15 for positioning the base element 5 or the connections 2A, 2B and 2C, and the distributor element 10, are shown in detail in FIGS. 3 and 4. As a suspension point, particularly for the drive motor 6, the drive elements 7, and the base element 5, there is a wall 17A, in which threaded bores are provided for, so that the aforementioned elements can be screwed onto the dividing wall using threaded screws.

The base or rotating element 5 is driven by the stepper motor 6 and a belt drive 8. A first, particularly a toothed, belt pulley 19 is fastened to the rotor shaft 18 of the stepper motor 6. A belt 20, preferably implemented as a toothed belt, conveys the drive motion of the stepper motor 6 from the first belt pulley 19 to a second, particularly a toothed, belt pulley 21, which is connected to a shaft 9. The shaft 9 is supported on two bearing points, wherein, for example as shown in FIG. 4, one bearing point is formed by the dividing wall 17, and the other bearing point by the distributor 10. Preferably a ball bearing 25 is provided for on the bearing point formed by the wall 17A. One end of the shaft 9 projects through a bore in the dividing wall 17 into the cleaning or care chamber 4. At this end of the shaft 9 a threaded bore 22 is provided for, into which a threaded pin 23, penetrating the rotating element 5, can be inserted, to connect the shaft 9 with the rotating element 5 and the connections 2A, 2B and 2C. The threaded bore 22 and the threaded pin 23 are covered by a cap 24 that can be fastened onto the rotating element 5.

The distributor 10 to supply connections 2A, 2B and 2C with cleaning or care agents is constructed in two parts. It comprises a first distributor part 10A that can be moved with the base element 5 relative to the supply device 3, and a second distributor part 10B that is fixed or immobile relative to the supply device 3. Both distributor parts 10A and 10B have a bore roughly in the center of them to hold shaft 9. In the bore in the distributor part 10B there is, furthermore, a bearing, particularly a slide bearing, for shaft 9.

The second distributor part 10B is incorporated or fastened into a recess in the wall 17A. It has at least one, preferably multiple, lines 12 for cleaning or care agents that are connected to the supply device 3, so that the cleaning or care agents can pass over from the supply device 3 into the lines 12. For example, FIG. 4 shows how line 3A of the supply device 3 passes through the wall 17A in order to reach the receiving aperture of the line 12 located on a surface of the second distributor part 10B. The line 12 penetrates the second distributor part 10B and forms a dispensing opening on a surface of the second distributor part 10B facing the first distributor part 10A, through which the cleaning or care agent can be dispensed from the second distributor part 10B onto the first distributor part 10A. The dispensing opening of said one line or the dispensing openings of the multiple lines 12 define a single interface or transition point 28 on the surface of the second distributor part 10B.

The first distributor part 10A is incorporated into a receptacle 32 (see FIG. 5) of the base element 5. It has at least one separate line for each of the connections 2A, 2B and 2C. According to the embodiment shown in FIG. 6, three separate lines 11A, 11B and 11C are provided for in the first distributor part 10A for each connection 2A, 2B and 2C, wherein for each connection 2A, 2B or 2C the line 11A conveys a cleaning agent, line 11B compressed air, and the line 11C a lubricant. Each of the lines 11A, 11B and 11C penetrates the first distributor part 10A, and thus has on the surfaces of the first distributor part 10A a receiving opening for the cleaning or care agent facing the second distributor part 10B, and a dispensing opening for the cleaning or care agent which faces the connections 2A, 2B and 2C. The cleaning or care agents reach the different connections 2A, 2B and 2C from the dispensing openings, particularly through bores or lines 26A and 26B in the base element 5. Said at least one line or the multiple lines 11A, 11B and 11C that are each assigned to one of the connections 2A, 2B and 2C define another interface or transition point at their receiving openings. According to the embodiment in FIG. 6, there are therefore three transition points 27A, 27B and 27C for the three connections 2A, 2B and 2C, wherein each transition point 27A comprises the three receiving opening of the three lines 11A, 11B and 11C for a connection 2A, 2B or 2C.

Through the movement, particularly the rotation, of the first distributor part 10A connected to the base element 5 relative to the second distributor point 10B that does not rotate relative to the base element 5 or the connections 2A, 2B and 2C, the receiving opening and lines 11A, 11B and 11C of the first distributor part 10A can be connected to said at least one line 12 and its dispensing opening in the second distributor part 10B. In particular, said at least one line or the multiple lines 11A, 11B and 11C of a connection 2A, 2B or 2C are connected or coupled with said at least one line 12 of the second distributor part 10B, so that such a connection 2A, 2B, 2C can be supplied with a cleaning or care agent, while the lines 11A, 11B, 11C of the other connections 2A, 2B, 2C are not connected or coupled with said at least one line 12 of the second distributor part 10B, and therefore cannot be supplied with a cleaning or care agent. According to the embodiment in FIG. 6, one of the three transition points 27A, 27B, 27C of the first distributor part 10A is connected to the only transition point 28 of the second distributor part 10B, or these two transition points overlap, while the other two transition points 27A, 27B, 27C of the first distributor part 10A are not simultaneously connected to the transition point 28 of the second distributor part 10B. Thus, only one of the three respective connections 2A, 2B, 2C can be supplied with a cleaning or care agent, wherein, by rotating the base element 5, each of the three connections 2A, 2B, 2C can be sequentially connected to the transition point 28, and thus permit the sequential supply of the three connections 2A, 2B, 2C during one cleaning or care cycle.

Figure 6:
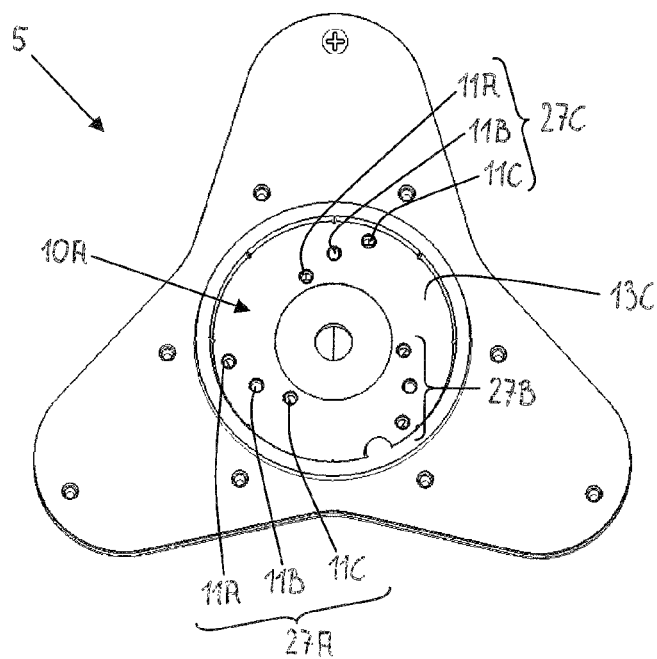
FIG. 6 shows a view from above onto the back of the base element from FIG. 5 facing the supply device, including the first distributor part of the distributor, separate from the cleaning or care device.

As can furthermore be seen from FIGS. 4 and 6, the first distributor part 10A and the second distributor part 10B are disk-like in shape, wherein each distributor part 10A, 10B has an external sheath surface 13A, 14A and two covering surfaces 13B, 13C, as well as 14B, 14C. The two distributor parts 10A, 10B are arranged slidingly onto one another via one covering surface 13C, 14B each. Accordingly, the transition points 27A, 27B, 27C, 28 with their respective lines or openings are also provided on these two covering surfaces 13C, 14B. The two sliding surfaces 13C, 14B thus also form a sliding bearing, on which the rotating element is mounted rotatabely.

The detector unit 15 for positioning the base element 5 in a predefined starting position comprises a mark 16 on one of the drive elements 7 and a sensor 17 that detects the mark 16. According to the embodiment shown in FIG. 4, the detector unit 15 also has a radiation or light source (not shown) that emits radiation in the direction of the sensor 17, designed as an optical sensor, wherein the mark 16 is located between the optical sensor 17 and the radiation or light source. The mark 16 is designed as a projection or pin that is immovably fastened to the shaft 9, and rotates along with the shaft 9. The starting position is defined as that position in which the mark 16 is located in such a way that it weakens or interrupts the beam emitted by the radiation or light source, so that the radiation reaching the sensor 17 is at least significantly reduced. If the mark 16 is located in the starting position, then the connections 2A, 2B, 2C likewise fixed to shaft 9 assume a predefined position.

The sensor 17 is connected to the control system 19, and emits position signals that reflect the position of the mark 16, and thus that of the connections 2A, 2B, 2C. The control system 19 is configured to drive the drive motor 6 and the shaft 9 until the starting position is reached. When the starting position is reached, the control system 19 stops the drive motor 6, so that the connections 2A, 2B, 2C take up their predefined position. Taking this position as a starting point, it is ensured that each of the connections 2A, 2B, 2C can be reliably connected to the supply device 3, by the control system 19 specifying a predetermined step sequence or number of steps to the stepper motor 6. The starting position is preferably taken up prior to the cleaning or care agents starting to be dispensed to the connections 2A, 2B and 2C.

Figure 5:
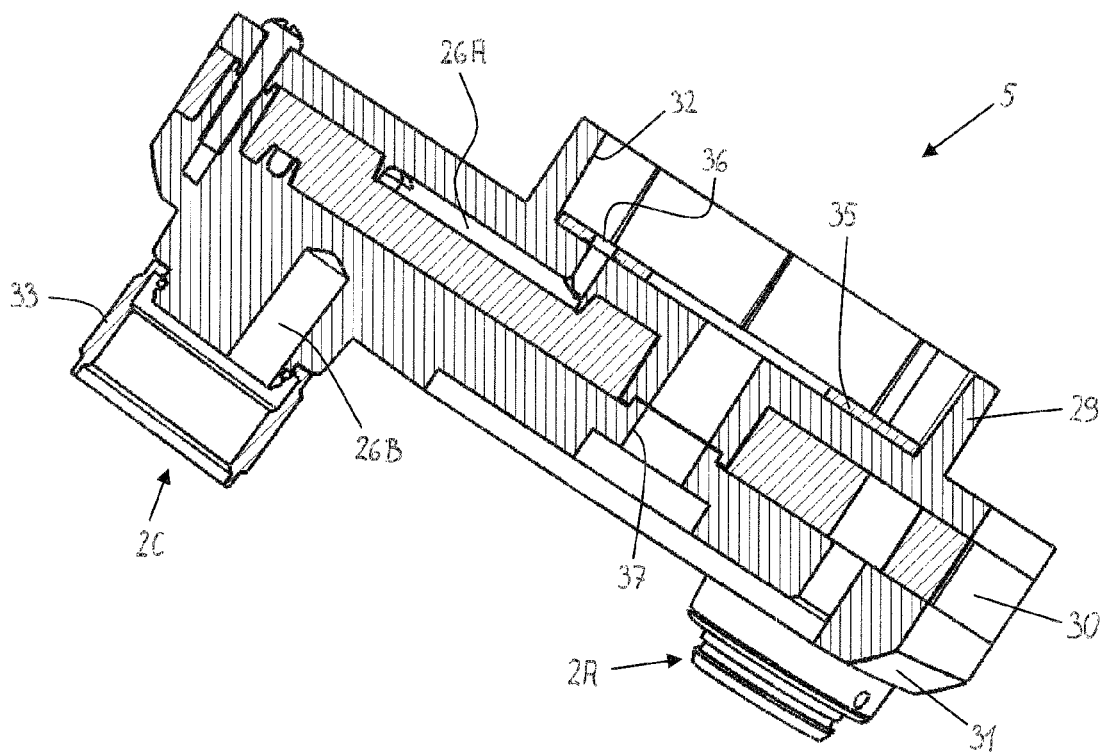
FIG. 5 shows a sectional representation of the base element shown in FIG. 4.

The structure of the base element 5 is particularly shown in FIGS. 5 and 6. The base element 5 comprises three layers: A back part 29, preferably manufactured from plastic, situated closest to the dividing wall 17; an adjacent sealing part 30, preferably manufactured from an elastomer; and a front part 31 adjacent to that, again preferably manufactured from plastic. The three parts 29, 30 and 31 are connected with one another by means of threaded pins screwed into corresponding threaded bores in the parts 29, 30, 31. The bore 37 through the base element 5 is used to incorporate the threaded pin 23.

The circular receptacle 32 for the first distributor part 10A is provided on the back part 29. In the receptacle 32 there is additionally a sealing disk 35. The three connections 2A, 2B, 2C are located on the front part 31, wherein preferably at least parts of the connections 2A, 2B, 2C are formed integrally with the front part 31. Furthermore, a metallic coupling sleeve 33, can be discerned on the connection 2C for the instruments to be coupled to connections 2A, 2B, 2C.

All three parts 29, 30, 31 of the base element 5 are penetrated by bores or lines 26A, 26B for conveying cleaning or care agents to the connections 2A, 2B, 2C, wherein at least one such line 26A, 26B is assigned to each connection 2A, 2B, 2C. These lines 26A, 26B end in the openings 34 of the connections 2A, 2B, 2C shown in FIG. 3. The supply lines of the instruments to be cleaned or cared for can be coupled to these openings 34 in such a way that the cleaning or care agent can get into the interior of the instruments, particularly into their supply lines. The lines 26A, 26B end in openings in the back part 29 (for example, an opening 36 can be seen in FIG. 5) that connect to the lines 11A, 11B, 11C of the first distributor part 10A, so as to be able to accept the cleaning or care agent from the first distributor part 10A.

The invention is not limited to the embodiments described here but instead comprises all embodiments which deploy or include the basic appropriate functional principle of the invention. In addition, any of the features of any of the embodiments described and illustrated here may be combined with one another.

What is claimed is:

1. A cleaning or care device for cleaning or caring for medical or dental instruments, comprising:
    a cleaning or care chamber in which at least two connections for the instruments to be cleaned or cared are provided, and
    a supply device for supplying said at least two connections with a plurality of cleaning or care agents, wherein each connection is configured to be connected to a medical or dental instrument such that a cleaning or care agent can be delivered from a connection to an interior of a medical or dental instrument, and wherein
    said at least two connections are movably connected to the supply device, and wherein said at least two connections can be moved to predetermined positions and relative to the supply device such that one of said at least two connections occupies a supply position in which it is connected to the supply device and supplied with all of the plurality of cleaning or care agents, while another of said at least two connections occupies a non-supply position in which it is not connected to the supply device and cannot be supplied with a cleaning or care agent.

2. A cleaning or care device according to claim 1, wherein said at least two connections are arranged on a common base element that can be moved relative to the supply device in such a way that one of said at least two connections occupies the supply position and is connected to the supply device, while another of said at least two connections occupies the non-supply position in which it is not connected to the supply device.

3. A cleaning or care device according to claim 1, wherein the at least two connections are among a plurality of three or more connections, wherein only one connection of the plurality of three or more connections is positionable in the supply position while all other connections of the plurality of three or more connections occupy non-supply positions.

4. A cleaning or care device according to claim 1, further comprising
    a drive motor located outside the cleaning or care chamber to move said at least two connections and the supply device relative to one another.

5. A cleaning or care device according to claim 2, comprising a drive motor which is configured to drive the base element and is connected via at least one drive element to the base element.

6. A cleaning or care device according to claim 2, further comprising
    a distributor provided between the base element and the supply device to convey a cleaning or care agent from the supply device to said at least two connections, wherein the distributor comprises a first distributor part that can be moved with the base element relative to the supply device and a second distributor part that is fixed relative to the supply device.

7. A cleaning or care device for cleaning or caring for medical or dental instruments, comprising:
    a cleaning or care chamber in which at least two connections for the instruments to be cleaned or cared are provided, and
    a supply device for supplying said at least two connections with a cleaning or care agent, wherein
    said at least two connections and the supply device can be moved relative to one another in such a way that one of said at least two connections can be connected to the supply device and supplied with a cleaning or care agent, while another of said at least two connections is not connected to the supply device and cannot be supplied with a cleaning or care agent, wherein said at least two connections are arranged on a common base element that can be moved relative to the supply device in such a way that one of said at least two connections is connected to the supply device, while another of said at least two connections is not connected to the supply device, a distributor provided between the base element and the supply device to convey a cleaning or care agent from the supply device to said at least two connections, wherein the distributor comprises a first distributor part that can be moved with the base element relative to the supply device and a second distributor part that is fixed relative to the supply device, and wherein the first distributor part comprises at least one separate line for each of said at least two connections.

8. A cleaning or care device according to claim 6, comprising a disk-shaped first distributor part and a disk-shaped second distributor part, wherein each distributor part comprises an external sheath surface and two cover surfaces, and wherein the two distributor parts are each arranged with one cover surface sliding onto one another.

9. A cleaning or care device according to claim 2, comprising a detector unit for positioning the base element in a predefined starting position.

10. A cleaning or care device according to claim 9, wherein the detector unit comprises a mark on a drive element connecting the drive motor to the base element and a sensor that detects the mark.

11. A cleaning or care device according to claim 1, comprising a detector unit to determine which of said at least two connections is occupied by a medical or dental instrument, and/or which of said at least two connections is not occupied by a medical or dental instrument, and to emit corresponding occupation signals, wherein the detector unit is connected to a control system that is designed, based on the occupation signals emitted by the detector unit, only to supply those of said at least two connections with cleaning or care agents to which a medical or dental instrument is connected.

12. A cleaning or care device according to claim 1, wherein nozzles located separately from said at least two connections are provided for dispensing a cleaning or care agent onto the outside of the medical or dental instruments.

13. A method for the cleaning or care of medical instruments, with a cleaning or care device having at least first and second connections for instruments to be cleaned or cared and a supply device for supplying the first and second connections with a plurality of cleaning or care agents, wherein each connection is configured to be connected to a medical or dental instrument such that a cleaning or care agent can be delivered from a connection to an interior of a medical or dental instrument, wherein the connections are movably connected to the supply device such that connections can be moved relative to the supply device, and wherein the method comprises:

connecting the first connection to the supply device to occupy a supply position;

supplying the first connection with the plurality of cleaning or care agents via the supply device while the first connection is in the supply position, wherein while the first connection is in the supply position and connected to the supply device, the second connection is disconnected from the supply device and maintained in a non-supply position in which it cannot be supplied with a cleaning or care agent; and moving the at least two connections to predetermined positions and relative to the supply device such that the second connection is in the supply position and the first connection is in a non-supply position.

14. A method for the cleaning or care of medical or dental instruments according to claim 13, wherein said at least two connections are successively positioned in the supply position and connected to the supply device and supplied by the supply device with the plurality of cleaning and/or care agents, so that at least a part of the cleaning or care method, in particular the cleaning or care of the interior of the medical or dental instruments is carried out sequentially.

15. A method for the cleaning or care of medical instruments according to claim 13, wherein only those of said at least two connections are connected to the supply device and supplied by the supply device with a cleaning and/or care agent that are occupied by a medical or dental instrument.

16. A method for the cleaning or care of medical or dental instruments according to claim 13, wherein the first and second connection are among a plurality of three or more connections, wherein only one of the plurality of three or more connections is positional in the supply position and in alignment with the supply device while all other connections of the plurality of three or more connections occupy the non-supply position.

17. A cleaning or care device according to claim 7, wherein the second distributor part comprises at least one line for a cleaning or care agent, wherein the motion of the first distributor part relative to the second distributor part can connect the lines of the first distributor part to said at least one line of the second distributor part.

* * * * *